United States Patent
Horstmann

[11] Patent Number: 5,902,601
[45] Date of Patent: May 11, 1999

[54] VOLATILE ACTIVE SUBSTANCE CONTAINING PLASTER THAT MAY BE PRODUCED WITHOUT SOLVENTS

[75] Inventor: Michael Horstmann, Neuwied, Germany

[73] Assignee: LTS Lohmann Therapie-Systeme GmbH, Neuwied, Germany

[21] Appl. No.: 08/959,541

[22] Filed: Oct. 24, 1997

Related U.S. Application Data

[63] Continuation of application No. 08/619,579, filed as application No. PCT/EP94/03107, Sep. 22, 1993, abandoned.

[30] Foreign Application Priority Data

Sep. 22, 1993 [DE] Germany .............................. 43 32 094

[51] Int. Cl.$^6$ .................................................. A61F 13/00
[52] U.S. Cl. ........................... 424/448; 424/443; 424/447; 424/449
[58] Field of Search ................................... 424/443, 447, 424/448, 449

[56] References Cited

U.S. PATENT DOCUMENTS

| | | | |
|---|---|---|---|
| 4,379,454 | 4/1983 | Campbell et al. | 604/897 |
| 4,915,950 | 4/1990 | Miranda et al. | 424/448 |
| 5,164,416 | 11/1992 | Nagai et al. | 514/763 |
| 5,306,502 | 4/1994 | Jaeger et al. | 424/443 |
| 5,462,746 | 10/1995 | Wolter et al. | 424/449 |
| 5,538,736 | 7/1996 | Hoffmann et al. | 424/448 |

FOREIGN PATENT DOCUMENTS

| | | |
|---|---|---|
| 0 249 475 | 12/1987 | European Pat. Off. . |
| 0321524 | 12/1988 | European Pat. Off. . |
| 94/03107 | 3/1995 | European Pat. Off. . |
| 3 629 304 | 3/1989 | Germany . |
| 3 231 400 | 1/1991 | Germany . |
| 3 743 946 | 6/1991 | Germany . |
| 4 210 165 | 2/1993 | Germany . |
| 88/10111 | 12/1988 | WIPO . |

Primary Examiner—Thurman K. Page
Assistant Examiner—Kathryne E. Shelborne
Attorney, Agent, or Firm—Wenderoth, Lind & Ponack, L.L.P.

[57] ABSTRACT

An active substance-containing adhesive patch with a pressure sensitive fixing device, containing at least one readily volatile ingredient, consisting of a substantially active substance-impermeable backing layer, at least two active substance-containing matrix layers and a removable protective layer, whereby the matrix layer containing the readily volatile active substance is laminated on a separately produced composite of one or more further matrix layers which are active substance-free, is characterized in that the first active substance-containing matrix layer consists of a spreadable molecularly disperse solution of the matrix base material in the readily volatile ingredient as the exclusive solvent, the composite which is obtained after laminating forming an active substance matrix that is as a whole shear-resistant after migration of the readily volatile ingredient into the composite.

15 Claims, 3 Drawing Sheets

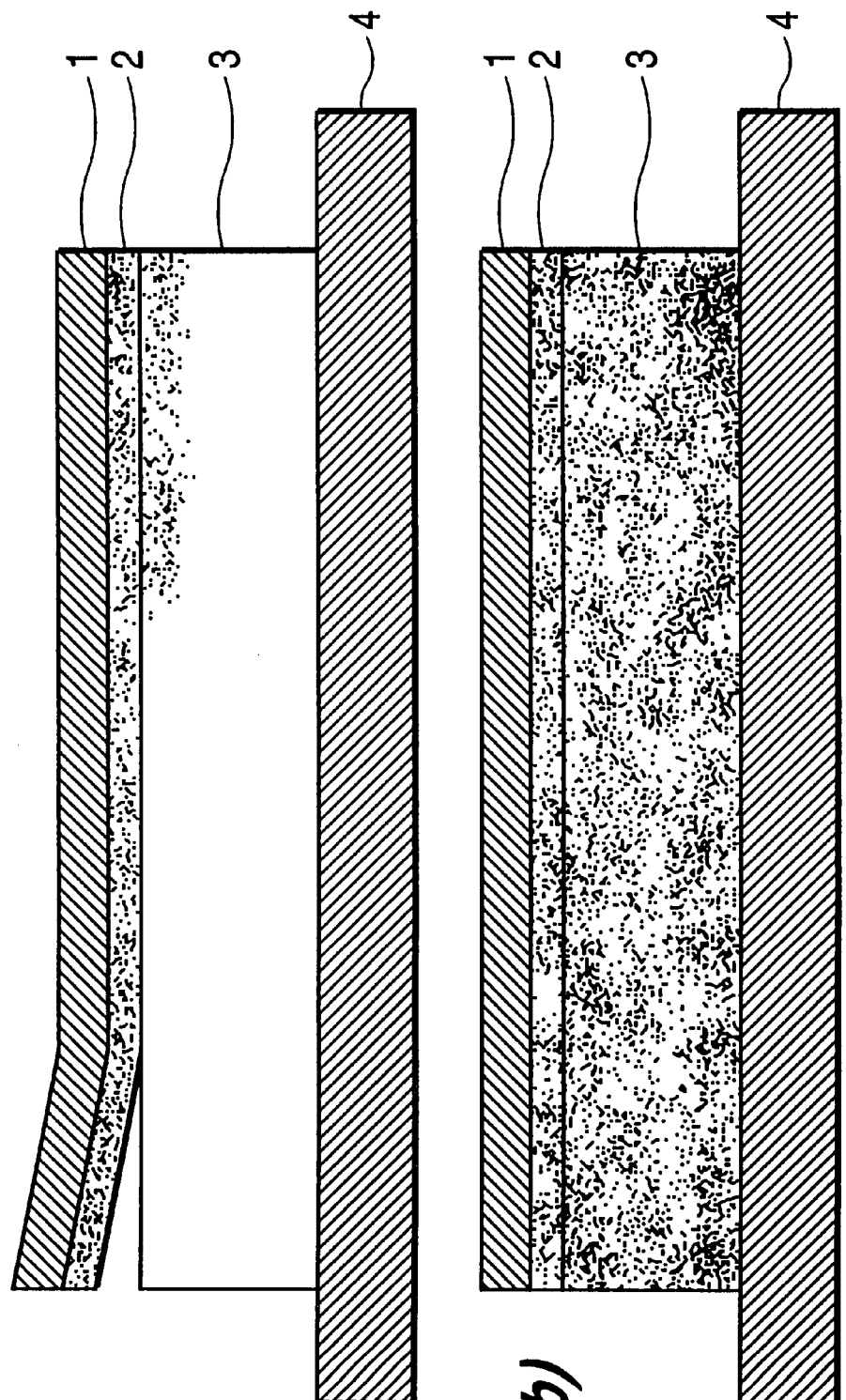

VOLATILE ACTIVE SUBSTANCE CONTAINING PLASTER THAT MAY BE PRODUCED WITHOUT SOLVENTS

This application is a continuation of now abandoned application Ser. No. 08/619,579, filed Mar. 22, 1996, which application is a U.S. National Stage application of International Application No. PCT/EP94/03107, filed Sep. 22, 1993.

This invention relates to an active substance-containing adhesive patch for the release of active substances via the skin to the human body.

BACKGROUND OF THE INVENTION

Active substance-containing adhesive patches have already been introduced on the market under the special designation transdermal therapeutic systems (TTS) and have been used in the therapy of a number of diseases.

Many of the active substances that are particulary suited for transdermal therapy are already perceptibly volatile at room temperature, or at least at the usual processing temperatures of 60 to 80° C. This is disturbing since, due to the hardly foreseeable degree of active substance loss during the process in each individual case, it is not possible to achieve a safe dosage of the pharmaceutic agent. Volatility, as understood by the instant invention, is present in any case if from a shallow vessel which is filled with an excess of the pure substance covering the base of the vessel, at 100° C. at least 0.1 mg substance per hour is continuously released to the environment per 10 $cm^2$ of free surface. In particular cases, as with highly effective pharmaceutical agents, which in TTS are typically dosed at surface concentrations of around 1 mg per 10 $cm^2$, or less, even slight volatility can be disturbing. For this reason the above definition can only serve as a rough guideline.

The problem of volatility also concerns readily volatile ingredients in TTS which have no therapeutic effect themselves but which have the function of increasing the active substance flow through the skin. Substances suitable for this purpose are for example: benzyl alcohol, butanol and other short-chain alcohols, triglycerides, high-boiling aliphatic hydrocarbons, glycerin, glycerin monooleate, isopropyl myristate or other short-chain esters, menthol or other volatile terpene derivatives (which are mixture components of a great number of natural essential oils), octanol-1 and other volatile medium-chain alcohols (e.g. oleyl alcohol), octanoic acid and other medium-chain aliphatic carboxylic acids, and many other substances.

This problem with regard to manufacturing technology, which is common to all volatile active substances and auxiliary substances (described in summary as "readily volatile ingredients" in the following) has lead to a plurality of proposals of—mostly rather complicated—constructions for TTS containing such additives. For example, a rather large quantity of ethanol is stored along with the active substance (which in this case is non-volatile) in a bag-type reservoir; during use the auxiliary substance as well as the active substance pass through a control membrane (U.S. Pat. No. 4,379,454).

Since for the user a thin, flexible construction is important, it was desirable to realize the addition of readily volatile additives in more simple adhesive patches as well—in the ideal case consisting only of a self-adhesive matrix layer and a non-adhesive backing layer. This has indeed been frequently suggested. DE-OS 42 10 165, for example, describes simple matrix TTS with an added amount of polar and nonpolar penetration enhancers.

According to this classical technique, matrix TTS, and also such matrix TTS containing readily volatile ingredients which are to remain in the pharmaceutic product, are produced in by a method in which a solution of the adhesive is mixed in a low-boiling solvent with the active substance and the volatile ingredient, the mixture is applied in the form of a film to a base film/sheet, the volatile solvent is removed by heating (in most cases up to 50 to 80° C.) and the thus-obtained product is covered with a removable protective foil. In this process, solvents suitable for dissolving the adhesive are used—i.e. such solvents as are even more readily volatile than the ingredients which have been added to the system to be retained therein—for example, methanol, ethanol or isopropanol, benzene, acetone, ethyl acetate etc.

Many of the additives mentioned in DE-OS 42 10 165, for example pinene and limonene, however, are, under these conditions, so highly volatile that it is not possible to achieve a reproducible dosage with the described single-layer system structure and the described process.

In an alternative production procedure, the hot-melt process, such as described in DE 37 43 946 for the transdermal application of nitroglycerin, such problems occur at a lesser extent since active substance and auxiliary substances are melted together in a closed system and come into contact with the ambient air only for a short time, after coating. On the other hand, a number of auxiliary agents and active substances are not suitable for this process because the auxiliary substances are not sufficiently thermoplastic, the active substances are too temperature-sensitive, or because the added amount of plasticizing but volatile auxiliary substances is too small to ensure process temperatures that are sufficiently low.

The possibility of introducing a piece of nonwoven printed with volatile active substance, e.g. nicotine, solves the problem of evaporation; however, this leads to comparatively thick active substance adhesive patches.

DE 32 31 400 makes use of the migration of active substances or adjuvants between matrix layers, in order to prevent the recrystallization of active substance and adjuvant. However, this document only describes matrix layers that have each been enriched with active substance or auxiliary substance, which matrix layers—after laminating and migration—result in a TTS exhibiting advantageous active substance flow. No mention is made therein of the use of the active substance or adjuvants themselves as solvents which can be employed at room temperature. Accordingly, the advantages of the migration process for obtaining shear-resistant TTS having volatile ingredients has not been realized in this document.

EP 0 249 475 describes a delivery system consisting of component parts which are to be joined immediately prior to use. After the combination thereof, the active substance migrates from the active substance-containing layer into the layer that is initially entirely free of active substance. This results in a desired retardation of the release. In this system no migration of the active substance has occurred at the point in time when the system is applied for therapeutic treatment. Thus, the system described in the above document does not show the advantages with regard to therapy and application technology of a system where at the time of application a migration has already occurred. The retardation of the active substance release described in the system according to EP 0 249 475 in most cases is not desired. Moreover, the system according to EP 0 249 475 is further disadvantageous in so far as it does not contain any teaching as to how to proceed with readily volatile active substances;

consequently it does not describe how such substances can be dosed accurately in transdermal systems.

DESCRIPTION OF THE INVENTION

The concept of utilizing the migration of ingredients in general is known. DE-PS 36 29 304 describes the dosage of volatile active substances onto an absorptive substrate which has a smaller surface, which substances are subsequently—prior to application—distributed within the adjacent matrix layers by migration.

A modification of this technique, applied to all-over laminates, can be found in U.S. Pat. No. 4,915,950. Here, the ingredient—which may also be a volatile substance, for example an essential oil—is applied to a porous, absorbent substrate by printing; from this substrate the ingredient is subsequently—prior to application—distributed by migration in the adjacent matrix layers. It is true that this system does have some advantages, such as the avoidance of evaporation of active substance during production, which can have consequences with regard to labour protection. However, the composition of the resulting TTS is still rather complicated and a textile or otherwise porous intermediate layer leads to an undesirable rigidity with the possible consequence of the system having a poorer tackiness to the skin.

It is therefore the object of the present invention to provide an active substance-containing adhesive patches that enables an almost loss-free incorporation of active substances or auxiliary substances which are volatile at the usual processing temperatures, has a simple structure and has improved wearing properties on the skin.

This object is achieved according to the present invention by an active substance-containing adhesive patches having a layered structure, consisting of a backing layer which is substantially active substance impermeable, at least two active substance-containing matrix layers and a removable protective layer, the matrix layer, which contains the readily volatile active substance, being laminated on a separately produced composite of one or more further matrix layers, characterized in that, during production, the first matrix layer constitutes a spreadable molecular-disperse solution of the matrix base material with the readily volatile ingredient as the exclusive solvent, and in that the composite obtained after laminating subsequently becomes sufficiently shear-resistant after the migration of the readily volatile ingredient, as is required for use as an active substance adhesive patch.

A basic thought of the invention is on the one hand the division of the matrix layer into two parts that are to be laminated on top of each other, one of which consists of a matrix layer with the readily volatile ingredient and an active substance-impermeable foil. It is characterizing in this connection that during the manufacturing process this "first matrix layer" (2 in FIG. 1) is a spreadable, molecular-disperse solution of the matrix base material with the readily volatile ingredient as the exclusive solvent. Since the other sections of the TTS (3 in FIG. 1), which are accessible to the readily volatile ingredient through migration, are formed such that they are very absorptive to the readily volatile ingredient and, in principle, have in addition a greater thickness than the first matrix layer, the spreadable-viscous consistency of this layer disappears shortly after manufacture—the system as a whole becomes soft-tacky but remains, as a whole, dimensionally stable.

Generally during production, the first matrix has a thickness between 2 and 100 μm, preferably 10 to 30 μm. In addition, the first matrix layer has, during production, at least 40% wt. of the readily volatile ingredient.

Whereas the other parts of the TTS can be produced conventionally by solvent drying, by hot-melt techniques or even by coating with a dispersion of adhesive in water, for the production of the "first matrix layer" the mostly polymeric auxiliary substances are dissolved at a higher proportion of the readily volatile ingredient and are applied to one of the two process films or sheets (removable protective film or final backing layer) by means of exactly controlled application techniques. In this connection thin film techniques, inter alia wire doctor knife application, are to be mentioned in particular. It is important that a prolonged open storage of this matrix layer is avoided, since otherwise there is the threat of evaporation. Ideally lamination onto the already pre-fabricated remainder of the matrix, which generally has a greater thickness, takes place immediately following the coating. After that, migration of the readily volatile component takes place so that the enriched section loses its extreme plasticity and the matrix as a whole acquires a shear-resistance which meets the therapeutic requirements. The duration of this process is dependent—apart from other physical parameters—on the diffusion properties of all the ingredients as well as on the overall geometry; usually the process is completed after a few minutes up to several hours. In isolated cases a maturing time of several days or even weeks may be accepted. This is possible where TTS have a very large thickness (above ca. 1000 μm total matrix thickness), the volatile ingredients are poorly diffusible and the ambient temperature is low.

Since, after lamination, the completed system is protected on both sides by impermeable films, this migration and maturing process can be intensified and accelerated by short exposure to heat. Usually, the systems are exposed to temperatures of 30 to 60° C. for 20 seconds to 30 minutes. By dividing the matrix into two sections, of which only one comprises the readily volatile component, the section which is free of this substance can initially be manufactured and provided in a conventional manner.

In principle, it is possible to position the layer which initially contains the readily volatile ingredient towards the skin (prior to use towards the removable protective foil), as shown in FIG. 2, but it is just as well possible to position this layer as shown in FIG. 1.

If the readily volatile ingredient has equal solubility in all matrix layers, after migration practically the same concentrations of the ingredient are found in all matrix layers (FIGS. 1 and 2). This is especially the case where the composition of the non-volatile ingredients is the same in all the layers used. However, it is also possible to achieve a different final concentration of readily volatile ingredient in each individual matrix layer by an appropriate selection of the solubilities in the individual matrix layers, if this is desired (FIG. 3).

A possible application of the construction principle according to the invention is in the form of an acetylsalicylic acid adhesive patch, or a pharmaceutically acceptable salt thereof, which acquires a particularly high skin permeability if the relatively high-volatile additive limonene is added. By using limonene, numerous polymeric base materials can be given a spreadable consistency.

Examples for readily volatile ingredients are the auxiliary substances 2-pyrrolidone, benzyl alcohol, butanol and other short-chain alcohols, cineole, diethylene glycol, diethylene glycol monoethyl ether, diisopropyl adipate, dimethyldecyl phosphoxide, dimethylisosorbide, dimethyllauroylamide, polydimethylsiloxane, dimethylsulfoxide, dodecylsulfoxide, acetic acid, ethyl acetate and other volatile aliphatic and aromatic esters (which are mixture components of numerous essential oils), ethylene glycol, ethylene glycol monolaurate and other esters and ethers of ethylene glycol or propylene glycol, 2-octyl dodecanol, glycerin, glycerin monooleate, glycerin monostearate, hydrogenated castor oil, isopropyl myristate, isopropyl palmitate, menthol or other volatile terpene derivatives (which are mixture components of numerous essential oils), methyl benzoate, methyl octyl sulfoxide, mono- or diethylacetamide, N,N-diethyl-m-toluamide, N-methylpyrrolidone, octanol-1 and other volatile medium-chain alcohols, octanoic acid and other medium-chain aliphatic carboxylic acids, oleyl alcohol, olive oil, oleic acid, oleic oleyl ester, phenyl ethanol, propylene glycol, ricinoleic acid, triacetin, but also mixtures of these substances, such as, for example, oleic acid/propylene glycol or limonene/dimethylisosorbide.

Examples for readily volatile pharmacological active substances are nicotin, nitroglycerin, salicylic acid, scopolamine, benzatropine, fenfluoramine, cyclopentamine, ephedrine and many others.

The base material of the first matrix layer can be identical with that of the other layers, it may also be clearly different, however. When all of the layers have an identical composition with regard to all of the non-volatile ingredients and after the migration of the readily volatile ingredients has terminated, the matrix obtained has a uniform monolithic composition. What is of critical importance is only that the skilled artisan takes the usual care over selecting the base materials in order to achieve laminatability.

Suitable materials for all matrix layers of the plaster according to the invention are therefore acrylic acid ester-containing copolymers, mixtures of rubbers and resins, polyvinyl acetate, silicone polymers and many other materials that can be applied to the skin without causing harm. Adding up to 40% fillers such as titanium dioxide, zinc oxide, chalk, activated carbon, finely distributed silicon dioxide, etc., does in no way impede the function according to the invention and can have advantages with regard to the cohesion of the fabricated systems.

DESCRIPTION OF THE DRAWINGS

The invention will be illustrated by way of example by FIGS. 1 to 3 and the examples of embodiments:

The FIGS. 1 to 3 each show a TTS comprising:
1. backing layer
2. a first matrix layer
3. a second matrix layer
4. removable protective layer in the state
    a) prior to migration
    b) following migration.

The figures show in more detail:

Figure 2A:
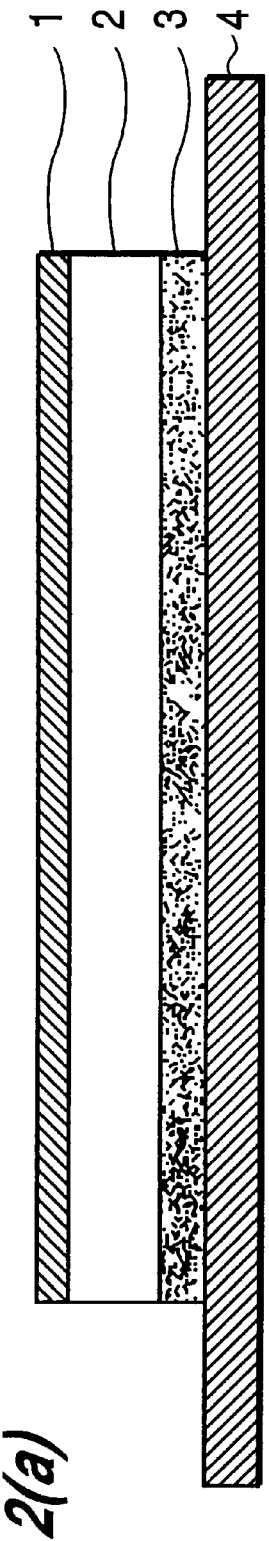
Figure 2B:
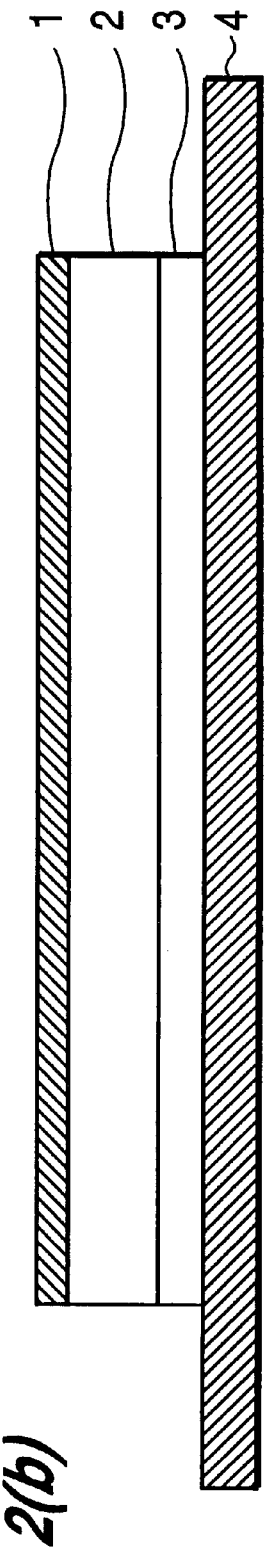
Figure 3A:
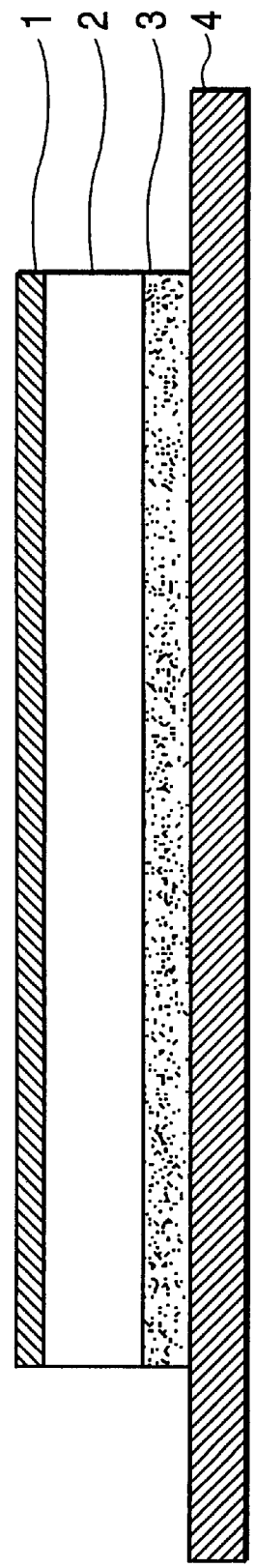
Figure 3B:
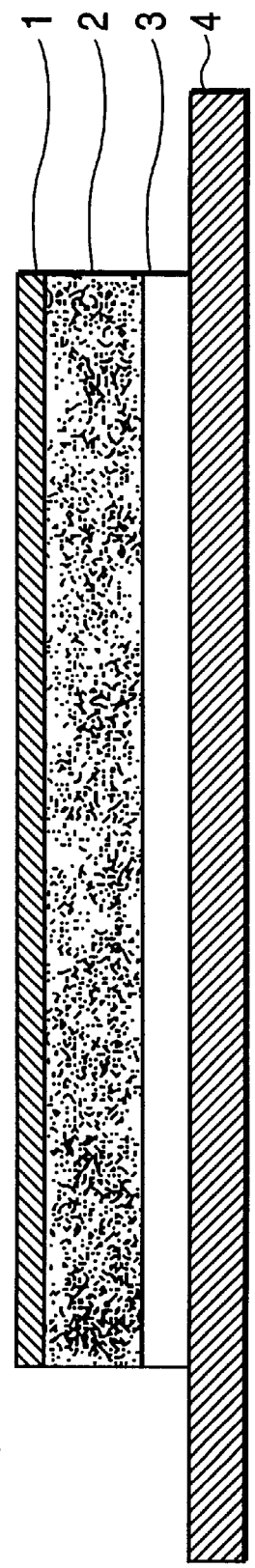

FIG. 1: layer with readily volatile ingredient, towards the skin; equal final concentration in the matrix layers after migration FIG. 2: layer with readily volatile ingredient, toward the removable protective layer; equal final concentrations in the matrix layers after migration FIG. 3: layer with readily volatile ingredient, towards the protective layer; different final concentrations of readily volatile ingredient in each matrix layer after migration

EXAMPLE 1

100 g solvent-free acrylate copolymer (Durotak 280–1753) and 1 g estradiol are dissolved in 300 ml peppermint oil while stirring, and coated onto a 15-$\mu$m-thick polyester film at a layer thickness of 30 $\mu$m. Immediately thereafter a composite of siliconized 75-$\mu$m-thick polyester film, coated with 200 g/m$^2$ acrylate copolymer (Durotak 280–1753), is laminated thereon, on the tacky side of each part. After 30 minutes of storage at room temperature, the finished laminate, after removal of the protective foil, shows excellent adhesive properties without smearing.

EXAMPLE 2

30 g styrene-isoprene copolymer, 20 g methyl ester of hydrogenated colophony and 50 g glycerol ester of hydrogenated colophony are dissolved in 120 ml of pure nicotin while stirring, and coated on a 21-$\mu$m-thick polyester film at a layer thickness of 40 $\mu$m. Immediately thereafter a composition of siliconized 100-$\mu$m-thick polyester film, coated under exposure to heat with 300 g/m$^2$ of a mixture of styrene-isoprene-copolymer/methyl ester of hydrogenated colophony/glycerol ester of hydrogenated colophony, is laminated thereon, on the tacky side of each part. After storing for 60 minutes at 40° C., the completed laminate shows excellent adhesive properties without smearing.

I claim:

1. An active substance-containing adhesive patch having pressure sensitive adhesive properties and containing at least one readily volatile ingredient, said patch consisting of a substantially active substance-impermeable backing layer, at least two active substance-containing matrix layers, and a removable protective layer, wherein
    a first matrix layer consists of a matrix base material and a readily volatile ingredient, which may be the active substance, present in an amount such that the first matrix layer is a spreadable mass,
    said first matrix layer is laminated together with a separately produced composite of one or more further matrix layers free of said readily volatile ingredient, but is absorptive to said readily volatile ingredient, to form a modified composite,
    said readily volatile ingredient is caused to migrate into the further matrix layer(s) of the separately produced composite, and
    said modified composite forms said active substance-containing matrix that is, as a whole, shear-resistant after migration of the readily volatile ingredient from the first matrix layer into the matrix layer(s) of the separately produced composite.

2. The active substance-containing adhesive patch according to claim 1, wherein the readily volatile ingredient is a pharmaceutically active agent.

3. The active substance-containing adhesive patch according to claim 1, wherein the readily volatile ingredient has properties enhancing the permeation of active substance into the skin.

4. The active substance-containing adhesive patch according to claim 1, wherein the matrix layer facing the skin has pressure-sensitive adhesive properties.

5. The active substance-containing adhesive patch according to claim 1, wherein the first matrix layer, during production, contains at least 40% wt. of the readily volatile ingredient.

6. The active substance-containing adhesive patch according to claim 1, wherein all matrix layers have an identical composition with regard to all the non-volatile ingredients and, after the migration of the readily volatile ingredient has terminated, a matrix is obtained having a uniform, monolithic composition.

7. The active substance-containing adhesive patch according to claim 1, wherein the first matrix layer, which contains the readily volatile ingredient, during production, has a lesser thickness than the other matrix layers.

8. The active substance-containing adhesive patch according to claim 1, wherein the first matrix layer, which contains the readily volatile active ingredient, during production, has a layer thickness of between 2 and 100 μm.

9. The active substance-containing adhesive patch according to claim 8 wherein the layer thickness is 10 to 30 μm.

10. The active substance-containing adhesive patch according to claim 1, wherein the readily volatile ingredient is a mixture of readily solvent substances.

11. The active substance-containing adhesive patch according to claim 1, wherein the active substance is acetylsalicylic acid or a pharmaceutically acceptable salt thereof.

12. The active substance-containing adhesive patch according to claim 10, wherein the main component of the said mixture of readily volatile substances is limonene.

13. A process for the production of an active substance-containing adhesive patch according to claim 1, wherein the first matrix layer, containing the readily volatile ingredient, is evenly applied to a removable protective layer, and a laminate consisting of a second matrix layer and a backing layer is laminated thereon to obtain a pharmaceutically active adhesive patch by migration of the readily volatile ingredient.

14. The process according to claim 13, wherein the composite obtained after lamination is subjected to a heat treatment to accelerate the migration.

15. The process according to claim 13, wherein the concentration of the readily volatile ingredient in the first matrix layer and the proportion of the first matrix layer to the second matrix layer is selected to obtain the required shear-strength of the matrix after migration.

* * * * *